United States Patent [19]
Grussmark

[11] Patent Number: 5,979,706
[45] Date of Patent: *Nov. 9, 1999

[54] COMBINATION DENTAL FLOSS DISPENSER AND STAND-UP TOOTHPASTE CONTAINER

[76] Inventor: Stephen M. Grussmark, 7400 N. Kendall Dr., Miami, Fla. 33156

[ * ] Notice: Under 35 U.S.C. 154(b), the term of this patent shall be extended for 652 days.

[21] Appl. No.: 08/642,184

[22] Filed: May 6, 1996

Related U.S. Application Data

[63] Continuation of application No. 08/430,391, Apr. 28, 1995, abandoned, which is a continuation-in-part of application No. 08/194,406, Feb. 10, 1994, abandoned.

[51] Int. Cl.⁶ .................................................. B65D 35/24
[52] U.S. Cl. .......................... 222/93; 222/105; 222/106; 222/556
[58] Field of Search .............................. 222/93, 105, 106, 222/107, 192, 156, 556; 132/309, 314, 321, 324, 325; 28/64

[56] References Cited

U.S. PATENT DOCUMENTS

| | | | |
|---|---|---|---|
| 811,370 | 1/1906 | Brush | 132/286 |
| 1,050,560 | 1/1913 | Moore | 132/192 |
| 1,439,076 | 12/1922 | Edwards | 132/314 |
| 1,466,982 | 9/1923 | Bailey | 222/192 |
| 1,488,810 | 4/1924 | Fraser | 222/192 Y |
| 1,492,836 | 5/1924 | Decker | 132/314 |
| 1,590,636 | 6/1926 | McManus et al. | 222/105 |
| 1,614,260 | 1/1927 | Siewert | 222/93 X |
| 1,733,114 | 10/1929 | Brennan | 222/192 X |
| 1,849,769 | 3/1932 | Priest | 132/311 |
| 1,858,134 | 5/1932 | Booth et al. | 222/93 |
| 2,078,149 | 4/1937 | Lutz | 222/105 |
| 2,084,568 | 6/1937 | White | 222/105 |
| 2,233,522 | 3/1941 | Fickle | 132/309 |
| 2,399,660 | 5/1946 | Boulicault | 132/311 |
| 2,511,038 | 6/1950 | Bergeron | 222/556 X |
| 2,601,244 | 6/1952 | Boulicault | 132/311 |
| 3,236,417 | 2/1966 | Linton | 222/92 |
| 3,342,379 | 9/1967 | Foley | 401/131 X |
| 3,353,714 | 11/1967 | Trecek | 222/107 |
| 3,741,447 | 6/1973 | Miles et al. | 222/517 |
| 4,428,389 | 1/1984 | Cordero | 222/93 |
| 4,470,521 | 9/1984 | Scammell | 222/556 X |
| 4,673,106 | 6/1987 | Fishman | 222/192 |
| 4,796,783 | 1/1989 | Paulson | 222/93 X |
| 4,801,054 | 1/1989 | Nycz | 222/556 X |
| 4,827,951 | 5/1989 | Grussmark | 222/192 |
| 4,934,389 | 6/1990 | Pettiford | 132/325 |
| 5,076,302 | 12/1991 | Chari | 132/325 |
| 5,228,595 | 7/1993 | Booker | 222/192 X |
| 5,271,536 | 12/1993 | Wilson | 222/556 X |
| 5,386,918 | 2/1995 | Neveras et al. | 222/556 X |

*Primary Examiner*—Kenneth Bomberg
*Attorney, Agent, or Firm*—Lloyd L. Zickert

[57] ABSTRACT

A combination dental floss dispenser and stand-up toothpaste container in which the dispenser is attached to the flip-open cap of the stand-up container, whereby the container, cap and dispenser are adapted to stand in the upright position on the dispenser.

12 Claims, 2 Drawing Sheets

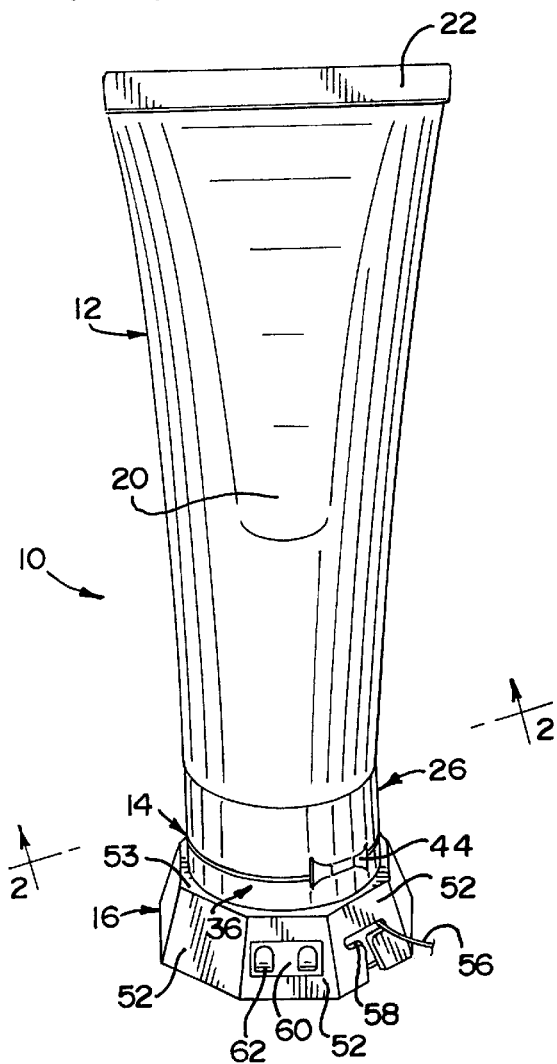
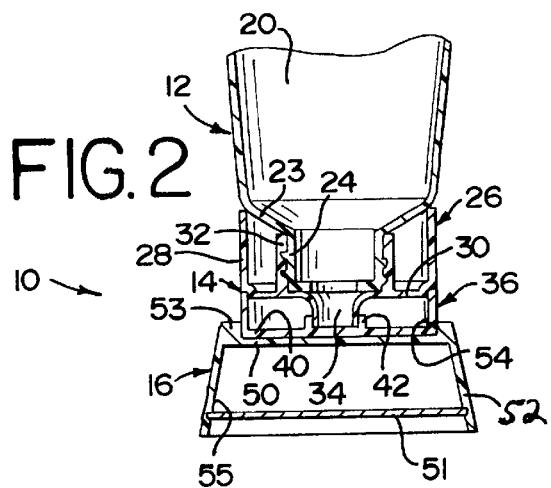
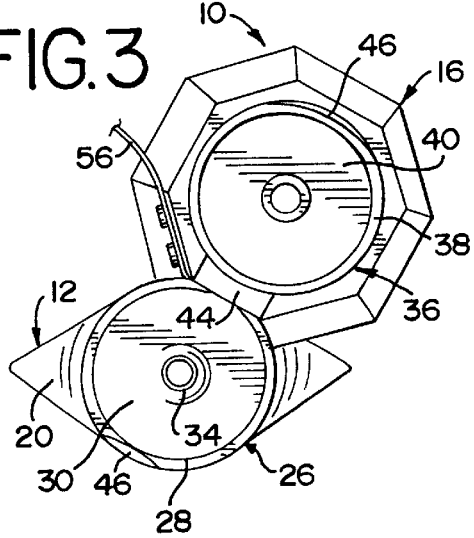
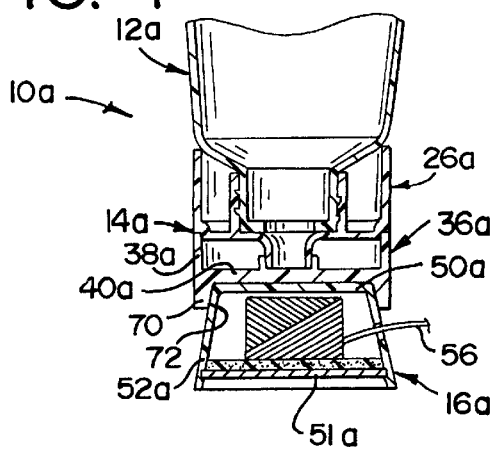
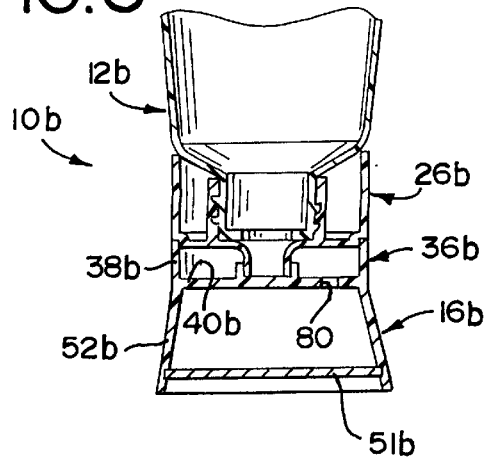

COMBINATION DENTAL FLOSS DISPENSER AND STAND-UP TOOTHPASTE CONTAINER

This application is a continuation of application Ser. No. 08/430,391, filed Apr. 28, 1995, now abandoned, which is a continuation-in-part of my copending application Ser. No. 08/194,406 filed Feb. 10, 1994, now abandoned.

This invention relates in general to a combination dental floss dispenser and stand-up toothpaste container, and more particularly to a dental floss dispenser secured to a flip-open cap or a screw-on cap that is mounted on a stand-up toothpaste tube, thereby providing a compact easily transportable device for convenient use in the teeth-cleaning process, and a device that stores in a stand-up position.

BACKGROUND OF THE INVENTION

Heretofore, it has been well known that flossing teeth is an important part of the teeth-cleaning process. Dentists highly recommend flossing at least once a day in conjunction with brushing to properly care for teeth and gums. While a large percentage of people brush daily, a much smaller percentage of people floss daily. This failure to floss daily leads to premature tooth decay and eventually the loss of teeth.

Numerous devices have been developed to remind and encourage people to floss during the brushing process. For example, dental floss dispensers have been attached to toothpaste containers in various forms. Exemplary of the type of devices heretofore known are disclosed in U.S. Pat. Nos. 1,858,134; 4,428,389; 4,673,106; and 4,827,951. These devices show dental floss dispensers attached to "standard" type toothpaste tube containers and "pump" type toothpaste tube containers.

The toothpaste industry has now developed a "new" flexible stand-up tube toothpaste container with a flip-open cap. This new stand-up container is significantly different from other containers because it is made from flexible plastic material and because the cap is constructed to form a base enabling the container to stand in an upright position. The industry has also developed a new stand-up container with a screw-on cap. No dental floss dispenser has been adapted to these types of containers to allow the container to still stand on its cap and contain the floss as well.

SUMMARY OF THE INVENTION

The present invention overcomes the above problem in providing a combination dental floss dispenser and stand-up toothpaste container in which the dispenser is attached to the flip-open cap or screw-on cap of a stand-up container such that the container, cap, and dispenser are adapted to stand in the upright position on the dispenser. The present invention is generally composed of a flexible stand-up toothpaste tube having a sealed tail at its upper end and a head at its lower end which includes a nozzle through which a charge of toothpaste may be dispensed.

With respect to the flip-open cap type, a two-part cap is attached to and coacts with the head to selectively open and close the nozzle, wherein the first part of the cap is removably attached to the nozzle to direct the flow of toothpaste through a spout, and wherein the second part of the cap is hingedly attached to the first part to seal or close the nozzle and spout in the closed position.

With respect to the screw-on cap type, the cap screws onto the nozzle to close the nozzle and prevent toothpaste dispensing.

A dental floss dispenser which includes a chamber for housing a spool of dental floss is adapted to be attached to either the second part of the flip-open cap or to the screw-on cap. The dispenser is provided with an opening through which the dental floss is threaded to withdraw a length of floss from the chamber, and also includes a cutter for severing the length of the floss from the dispenser.

Alternatively, with respect to the flip-open cap, the second part of the cap may include an opening and a cutter which coacts with the opening in the dispenser for withdrawing and severing the dental floss from the chamber. This further embodiment protects the end of the dental floss and reminds the user to floss when opening the cap for dispensing toothpaste. In all embodiments, the dispenser, cap, and container are adapted to stand in an upright position on the dispenser.

It is therefore an object of the present invention to provide a combination dental floss dispenser and toothpaste container wherein the latter is of the flexible stand-up tube type having a cap attached thereto, and wherein the dispenser and the container are adapted to stand in the upright position.

It is another object of the present invention to provide a compact combination dental floss dispenser and flexible stand-up toothpaste container for use in the teeth-cleaning process which stands in an upright position on the dispenser.

It is another object of the present invention to provide a combination dental floss dispenser and stand-up toothpaste container with a cap for opening the container to dispense toothpaste in which the dental floss is only accessible by opening the cap, thereby protecting the dental floss from contamination.

It is a further object of the present invention to provide a combination dental floss dispenser and stand-up toothpaste container which reminds the user to floss as well as brush his teeth for efficient cleaning of teeth.

Still a further object of the present invention is to provide a combination dental floss dispenser and flexible stand-up toothpaste container wherein the combination is provided with an opening to withdraw floss of a selected length and a cutter to sever the length from the dispenser.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a side perspective view of the combination dental floss dispenser and flexible stand-up toothpaste container of the present invention illustrating the placement of the dispenser on the flip-top cap of the container in the upright standing position;

FIG. 2 is a fragmentary sectional view of the combination dental floss dispenser and stand-up toothpaste container taken substantially through line 2—2 of FIG. 1 with some parts shown in elevation;

FIG. 3 is a bottom plan view of the combination dental floss dispenser and stand-up toothpaste container illustrating the floss dispenser attached to the flip-up cap in the open position;

FIG. 4 is a fragmentary sectional view of another embodiment of the combination dental floss dispenser and stand-up toothpaste container with a flip-top cap;

FIG. 5 is a fragmentary sectional view of a further embodiment of the combination dental floss dispenser and stand-up toothpaste container with a flip-top cap;

DESCRIPTION OF THE INVENTION

Figure 6:
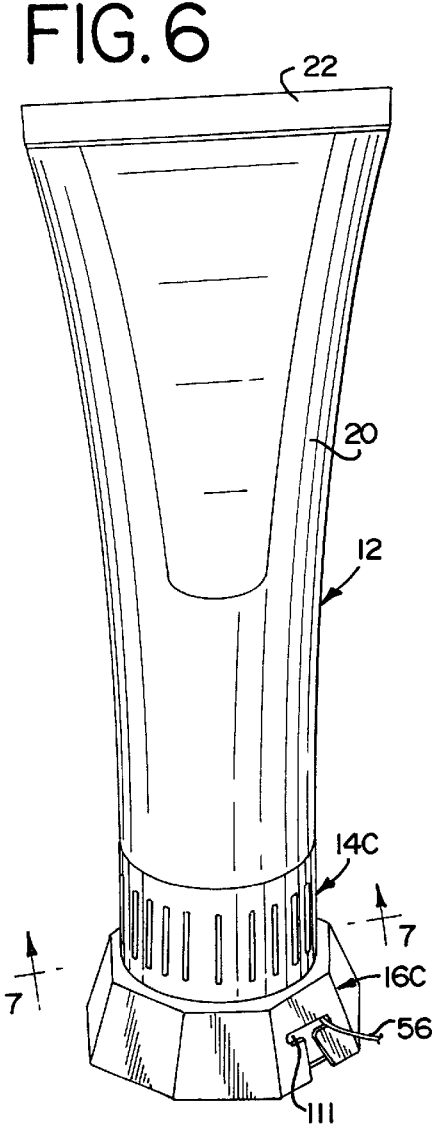
FIG. 6 is a perspective view of a further embodiment of the invention wherein a screw-on cap type container is fit into a socket of a floss dispenser.

Referring now to the drawings, and particularly to the embodiment of FIGS. 1 to 3, the combination dental floss dispenser and stand-up toothpaste container of the present invention, generally indicated by the numeral 10, is illustrated in the upright or standing position. As further shown in FIGS. 2 and 3, the combination dental floss dispenser and stand-up toothpaste container generally includes a flexible toothpaste tube 12, a two-part flip-up or flip-top cap 14 attached to the tube 12, and a dental floss dispenser 16 attached to the flip-up cap 14.

More particularly, the tube 12 includes a soft plastic elongated body 20 having a heat-sealed or pressure-sealed tail 22 at its upper end and a substantially rigid plastic molded head 23 at its lower end. The circular head 23 includes a nozzle 24 centrally positioned on the head 23. The tube 12 is adapted to be filled with toothpaste during the manufacturing process. In use, when the body 20 of the tube 12 is squeezed, toothpaste is forced through the nozzle 24 when the cap is removed or conditioned to dispense toothpaste. The nozzle 24 has an exterior threaded surface to facilitate attachment of the cap 14, as described below.

The two-part flip-open cap 14 includes a first part or member 26 which is adapted to attach to the head 23 of the tube 12 and a second part or member 36 hingedly attached to the first part. Member 26 includes a cylindrical exterior side wall 28 integrally attached to a circular bottom plate 30. The circular plate 30 includes a centrally positioned hollow cylindrical nut 32 sized slightly larger than the nozzle 24 and positioned internally within the exterior side wall 28. The nut 32 has interior threading adapted to threadedly engage the exterior threaded surface of the nozzle 24. This enables the cap 14 to be removably secured to or mounted on the head 23 of the tube 14 by twisting it off or on. The plate 30 further includes a centrally positioned spout 34 aligned with but on the opposite side of the plate 30 as the nut 32. The spout 34 directs toothpaste through the first member 26 of the cap 14 when the tube 12 is squeezed. It should be appreciated that the shape of the first and second parts of the cap could vary.

The second part or member 36 of the cap 14 is adapted to close the spout 34. Like member 26, member 36 includes a cylindrical exterior side wall 38 integrally attached to a circular base plate 40. The circular base plate 40 includes a centrally positioned hollow cylindrical socket 42 sized slightly larger than the spout 34 and positioned internally within the exterior side wall 38. The socket 42 is adapted to be received over and to close spout 34. Second member 36 is attached to the first member 26 by hinge 44 and is adapted to move between an open position as shown in FIG. 3 and a closed position as shown in FIGS. 1 and 2. In the open position, toothpaste may be dispensed through the spout 34 of cap 14, while in the closed position, the socket 42 and base plate 40 coact to close the spout 34, thereby preventing toothpaste from being dispensed through the nozzle 24 and the spout 34. The first and second parts 26 and 36 of the cap 14 have aligned finger indentations 46 on the outer surfaces of the cylindrical side walls 28 and 38 for providing easy opening of the second member 36.

The tube 12 and. the cap 14 are balanced and adapted to stand in the upright position on the base plate 40 of the second part of the cap 14 when placed on a substantially horizontal surface. This is important for storage purposes, for enabling gravity to work to maintain the toothpaste adjacent to the nozzle of the cap as the tube empties, as well as for the overall look and consumer acceptance of this packaging.

The dental floss dispenser 16 of the present invention includes a top wall 50, a bottom wall 51, and a plurality of side walls 52 defining a chamber for storing dental floss 56. The side walls 52 have an upper peripheral lip 53 which extends above the top wall 50, thereby defining a recess area 54 in the top of the dental floss dispenser 16. The dispenser 16 is of a suitable size such that the recess area 54 is sized so that the base plate 40 and the cylindrical wall 38 of the second part 36 of the cap 14 will be securely received by a suitable press-fit relation in the dispenser 16. Further, it may be appreciated that the floss dispenser may be attached to the toothpaste container by screw-threading the mating portions, employing a magnetic device, or using any suitable attaching means. The dispenser 16 may be removed from the second part of the cap by the user if desired. This construction enables the combination dispenser, cap, and tube to stand in the upright position on the dispenser when the cap is in the closed position. In this embodiment, the dispenser 16 should be of a suitable diameter for maintaining the container in the upright position, which will generally be larger than the typical dental floss dispenser.

The top wall 50, bottom wall 51, and side walls 52 of the dispenser 16 define a chamber 55 within which is disposed dental floss 56 preferably wound in some type of compact shape or on a spool (not shown). The dental floss 56 extends from an opening or a T-shaped cutout 58 in one of the side walls 52 of the dispenser 16. The exterior surface of the bottom wall 51 may include a cutting plate similar to a conventional dispenser. Alternatively, a cutter plate 60 may be attached to one of the side walls 52, as shown in FIG. 1, or may be attached to the exterior of wall 38 of the second part 36 of the cap 14 or the exterior of the wall on the first part 26. The cutter plate 60 generally includes two conventional tabs 62 that protrude from the cutter plate 60 and have cutting edges that are adapted to cut the dental floss 56 when the floss is pulled against a cutting edge.

A further embodiment of the combination dental floss dispenser and stand-up toothpaste container of the present invention, generally indicated by numeral 10A, is illustrated in FIG. 4. In this embodiment, the tube 12a is identical to tube 12 in FIGS. 1 to 3, and cap 14a is substantially identical to cap 14, except that the cylindrical wall 38a on the second member 36a includes a peripheral lip 70 which extends downwardly beyond the base plate 40a thereby defining a recess area 72 with the bottom of the base plate 40a in the second part 36a of the cap 14a. The dental floss dispenser 16a is similar to dental floss dispenser 16 except that it is smaller and that it does not have the peripheral lip 53. The top wall 50a and the side walls 52a of the dispenser 16a are adapted to be matingly and tightly received in the recess area 72, thereby removably attaching the dispenser 16a to the second part 36a of the cap 14a.

A still further embodiment of the combination dental floss dispenser and stand-up toothpaste container of the present invention, generally indicated by numeral 10B, is illustrated in FIG. 5. In this embodiment, the tube 12b is identical to tube 12 in FIGS. 1 to 3, and cap 14b is substantially identical to cap 14, except that the cylindrical wall 38b on the second member 36b is integrally formed with the side walls 52b of the dispenser 16b. Accordingly, dispenser 16b is not removable from the cap 14b and constitutes a one-piece construction with the second member of the cap. It should also be appreciated that the side walls 52b of dispenser 16b will be sized to allow the container, cap, and dispenser combination to stand in the upright position.

In the embodiment of FIG. 5, a single wall 40b of the second part of the cap also serves as the top wall of the dispenser and includes an aperture 80 through which the dental floss extends such that the dental floss is only accessible when the second part of the cap is in the open position. In the embodiment of FIG. 5, a cutter plate may be positioned on the upper surface of the wall 40b or on the side wall 38b. This alternative embodiment protects the end of the dental floss when the cap is closed and additionally reminds the user to floss when the cap is opened to dispense toothpaste. It will be understood that this feature of having the floss exit the top wall of the dispenser can also be applied to the embodiments of FIGS. 1 and 4 by extending the aperture through the base wall of the second part of the flip-open cap.

Figure 7:
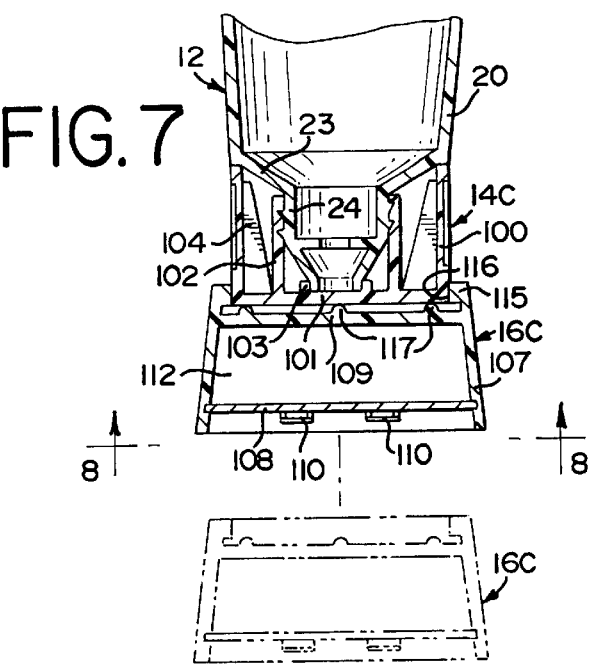
FIG. 7 is a fragmentary detailed sectional view taken substantially along line 7—7 of FIG. 6 and also illustrating the removability of the dispenser by showing it in phantom.
Figure 8:
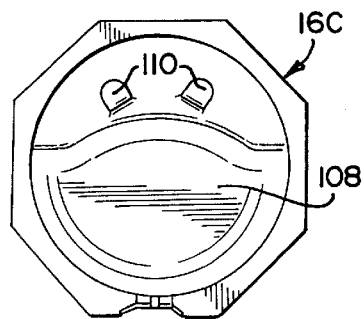
FIG. 8 is a bottom plan view of the dispenser taken substantially along line 8—8 of FIG. 7 and looking in the direction of the arrows.
Figure 9:
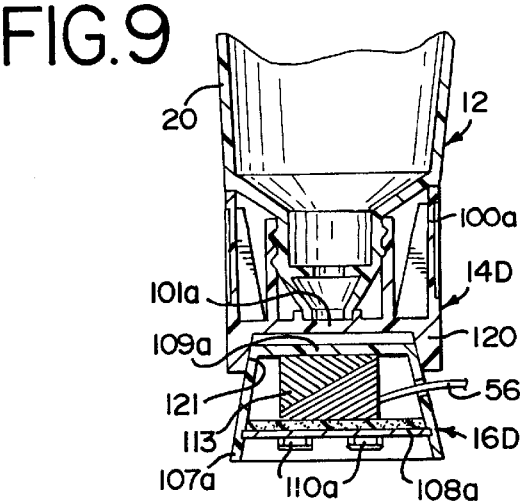
FIG. 9 is a sectional view like FIG. 7 of a still further embodiment with the dispenser being received within an opening or socket at the end of the cap of a container.
Figure 10:
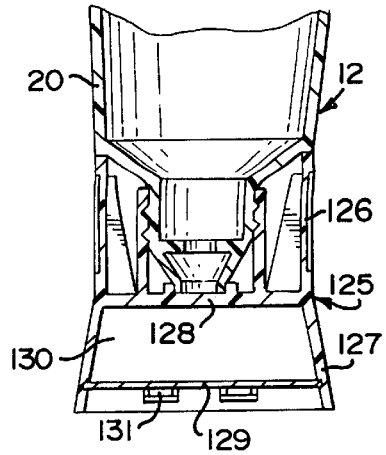
FIG. 10 is a vertical sectional view like FIG. 7 of a further embodiment wherein the floss dispenser is integrally formed with the screw-on cap.

The embodiment of FIGS. 6 to 8, as well as the embodiments of FIGS. 9 and 10, differ from the previous embodiments in that the toothpaste container is provided with a screw-on cap instead of a flip-top cap. This type of container requires unscrewing of the cap to expose the nozzle for dispensing toothpaste from the container. Otherwise, these embodiments are essentially the same as those with the flip-top cap inasmuch as a dental floss dispenser is removably attached to the cap.

With respect to the container having a flexible tube and nozzle for dispensing the toothpaste, the same numerals applied earlier are applied to these embodiments. The screw-on cap is generally designated by the numeral 14C and includes a generally outer cylindrical wall 100 that is fluted on the exterior surface to enhance gripping. An end wall 101 closes one end of the cylindrical wall 100. A cylindrical attachment wall 102 with internal threads to engage and screw on to external threads on the nozzle 24 extends inwardly from the inner side of the end wall 101. A stub wall 103 projects inwardly from the bottom wall 101 to mate with the tip end of the nozzle when the cap is screwed in place on the nozzle to close off the nozzle from dispensing toothpaste. A plurality of upstanding reinforcing ribs 104 radially spaced around the inner surface of the outer wall 100 serve to reinforce and strengthen the relationship between the outer wall 100 and the end wall.

The dental floss dispenser is generally indicated by the numeral 16C and includes an outer wall 107 made up of a plurality of slanting panels, a bottom wall 108, and a top wall 109. Dual cutters 110 are provided on the outer surface of the bottom wall 108 which serve to assist the user in cutting a suitable length of floss as it is dispensed from the container. While the cutters are normally placed on the bottom wall, they may be placed elsewhere if desired. As seen particularly in FIG. 6, an outlet opening 111 is formed in one of the panels in the side wall to allow the floss 56 to be dispensed. It will be understood that the floss is normally stored on a spool held within the compartment 112 such as the spool 113 shown in FIG. 9.

Extending upwardly from the top wall 109 of the dispenser is a retaining wall 115 defining a socket 116 into which the screw-on cap 14C snugly and frictionally fits, thereby interconnecting the dispenser to the cap. It should also be appreciated that the floss dispenser may be otherwise removably connected to the cap, such as by use of a screw-threaded connection. In this embodiment, the dispenser socket would have internal threads mating with external threads on the cap. The opposite threading arrangement would be used for the embodiment of FIG. 10.

Likewise, the embodiments of FIGS. 2 and 4 may utilize a screw-threaded connection. Spacers 117 are provided on the upper surface of the wall 109 of the dispenser for purposes of maintaining the end wall 101 of the cap in spaced relation to the wall 109 and also providing a stop against which the cap abuts when the dispenser and cap are joined together. As seen by the phantom view of the dispenser, it is removable from the cap so that it may be used independently of the toothpaste container, if desired. Normally, the dispenser will be mounted on the toothpaste container as illustrated in solid lines in FIG. 7 wherein the toothpaste container and the dispenser can be stored in an upright position with the bottom edge of the dispenser side wall 107 engaging the surface on which the container and dispenser will rest. Thus, the fit between the screw-on cap 14C of the toothpaste container and the socket 116 of the dispenser is such as to allow separation if desired but also to maintain the two units in joined together relation for storage and handling.

The embodiment of FIG. 9 differs from the embodiment of FIG. 7 in that the socket for joining a dispenser to the cap is formed on the cap rather than on the dispenser. The screw-on cap of FIG. 9 is generally designated by the numeral 14D, while the dispenser is generally designated as 16D. In this embodiment the dispenser includes a side wall 107a, a bottom wall 108a, and a top wall 109a. Cutters 110a are provided on the outer side of the bottom wall 108a. The side wall 107a may again be formed of a plurality of slanting panels although it may also be frustoconical in shape. In any event, the shape of the socket on the cap will be formed to mate with the body of the dispenser. The outer wall 100a of the cap 14D includes a retaining wall 120 extending from the end wall 101a and forming a socket 121 within which the upper end of the dispenser side wall 107a snugly and frictionally fits when the two are placed together. As in the embodiment of FIG. 7, the dispenser 16D may be removed from the socket of the screw-on cap if desired and used apart from the toothpaste container. While the footprint of the dispenser in the embodiment of FIG. 7 is greater than that of the end of the screw-on cap, the footprint of the dispenser in FIG. 9 is about equal to the footprint of the cap. In any event, the footprint of either embodiment is such as to facilitate the ability of the toothpaste container and the dispenser to stand on its end for storage purposes.

The embodiment of FIG. 10 differs from the embodiments of FIGS. 7 and 9 in that the screw-on cap and dispenser are integrally formed and the dispenser is not removable from the cap. Thus, opening of the toothpaste container of the embodiment in FIG. 10 for dispensing of the toothpaste is the only way that the floss dispenser can be removed from the toothpaste container. In this embodiment, the combination screw-on cap and floss dispenser, generally designated by the numeral 125, includes an outer wall having an upper generally cylindrical wall portion 126 and a lower generally frustoconical wall portion 127. However, it should be appreciated that the lower wall portion 127 may be defined by a plurality of flat slanting panels like the embodiments of FIGS. 7 and 9. A common wall 128 separates the screw-on cap portion from the dispenser portion, and a lower wall 129 closes off the dispenser to define a floss compartment 130. Again, as in the other embodiments, cutters 131 are provided on the under surface of the lower or bottom wall 129. A suitable opening will be provided in the side wall portion 127 for the floss to exit from the compartment 130 and be cut to size. However, the exit hole for the floss may be inside the cap as in the embodiment of FIG. 5, if desired. Similarly, the floss exit hole in the embodiments of FIGS. 7 and 9 may be in the top wall of the dispenser and the end wall of the cap as explained in the embodiments of FIGS. 1 to 5. In this embodiment, the toothpaste container and the floss dispenser will again serve to allow the container and dispenser to be stored in an upright position.

It will be understood that modifications and variations may be effected without departing from the scope of the novel concepts of the present invention, but it is understood that this application is to be limited only by the scope of the appended claims.

The invention is hereby claimed as follows:

1. A combination of a dental floss dispenser and a stand-up squeezable toothpaste container,
    said stand-up toothpaste container comprising:
        flexible tube means for storing toothpaste and a nozzle means at one end for selectively discharging toothpaste when a squeezing pressure is applied to said tube means, and
        a two-part cap means removably attached to said tube means, said cap means having a first part attachable to said nozzle means and a second part hingedly attached to said first part movable between open and closed positions for selectively opening and closing said nozzle means;
    said dental floss dispenser comprising:
        a housing means for storing dental floss, said housing means including a top wall, a bottom wall and side wall means, and means for dispensing and severing said floss from said housing, a footprint of said bottom wall being equal to or greater than a footprint of said top wall,
        means removably attaching the top wall of said dental floss dispenser to said second part of said cap means, and
        the bottom and side wall means of the dispenser being sized and formed such as to allow the combination container and dispenser to stand on a planar surface,
        whereby said combination dispenser and container are adapted to stand in an upright position on said dispenser.

2. The combination dispenser and container of claim 1, wherein said means attaching said dispenser to said second part of said cap includes a male member in one of said dispenser or cap, around a female member in the other of said dispenser or cap.

3. A combination of a dental floss dispenser and a stand-up squeezable toothpaste container,
    said stand-up toothpaste container comprising:
        flexible tube means for storing toothpaste and a nozzle means at one end for selectively discharging toothpaste when a squeezing pressure is applied to said tube means, and
        a two-part CELp means removably attached to said tube means, said cap means having a first part attachable to said nozzle means and a second part hingedly attached to said first part movable between open and closed positions for selectively opening and closing said nozzle means;
    said dental floss dispenser comprising:
        a housing means for storing dental floss, said housing means including a top wall, a bottom wall and side wall means, and means for dispensing and severing said floss from said housing, a footprint of said bottom wall being equal to or greater than a footprint of said top wall,
        said second part of the cap means having a portion interconnecting with said dispenser adjacent the top wall thereof,
        the bottom and side wall means of the dispenser being sized and formed such as to allow the combination container and dispenser to stand on a planar surface,
        whereby said combination dispenser and container are adapted to stand in an upright position on said dispenser.

4. A combination of a dental floss dispenser and a stand-up squeezable toothpaste container,
    said stand-up squeezable toothpaste container comprising:
        flexible tube means for storing toothpaste and having a nozzle means at one end for selectively discharging toothpaste when a squeezing pressure is applied to said tube means, and
        cap means coacting with the nozzle means for selectively opening and closing said nozzle means and being hingedly connected to said container,
    said dental floss dispenser comprising:
        a housing means for storing dental floss, said housing means including a top wall, a bottom wall and side wall means, means adjacent the top wall coacting with said cap means to removably attach said dispenser to said cap means by a press-fit relation, means for dispensing and severing said floss from said housing, and means adjacent the bottom wall enabling said housing means to stand on a planar surface,
        whereby said combination dispenser and container are adapted to stand in an upright position on said dispenser and said dispenser includes a footprint on which the dispenser may stand that is greater than the footprint of the cap means of the container.

5. A combination of a dental floss dispenser and a stand-up squeezable toothpaste container for dispensing dental floss and toothpaste,
    said stand-up toothpaste container comprising:
        flexible tube means for storing toothpaste and a nozzle means at one end for selectively discharging toothpaste when a squeezing pressure is applied to said tube means, and
        cap means removably attached to said tube means for enclosing said nozzle means,
        said cap means including means for screwing on the container to close the nozzle means,
    said dental floss dispenser comprising:
        a housing means for storing dental floss, said housing means including a top wall, a bottom wall and side wall, and means for dispensing and severing a length of said floss,
        means adjacent to said top wall of said housing interfitting with said cap means for removably mounting said dispenser on said cap means including socket means on said cap means for frictionally receiving the side wall of said dispenser, and the bottom and side walls of the dispenser being sized and formed such as to allow the combination container and dispenser to stand squarely on a planar surface, whereby said combination dispenser and container are adapted to stand in an upright position on said dispenser and the footprint of the bottom wall of the dispenser is greater than the footprint of the top wall thereof.

6. A dental floss dispenser and toothpaste container device for holding and dispensing dental floss and toothpaste comprising:

a stand-up toothpaste container including an elongated flexible tube having a sealed tail at an upper end and a head at a lower end including a nozzle through which toothpaste may be dispensed;

a two-part flip-open cap coacting with the head for selectively opening and closing said nozzle, said cap including a first part removably attachable to said head and a second part, said first part having a spout aligned with said nozzle on said head of said container to direct the flow of toothpaste from said nozzle through said spout and said first part of said cap, said second part being hingedly attached to said first part to facilitate movement of said second part between open and closed positions, said second part including closure means for engaging said spout in said closed position thereby preventing toothpaste from flowing from said spout, a dental floss dispenser having a housing including top, bottom, and side walls defining a chamber for storing dental floss, and an opening in the housing for dispensing floss;

means for severing said dental floss; and means for removably press-fit attaching said dental floss dispenser to said second part of said cap, whereby said container, cap, and said dispenser are adapted to stand in an upright position on said dispenser when said second part is in said closed position, and said dental floss dispenser may be selectively removed for use separate from the toothpaste container, and said dispenser includes a footprint on which the dispenser may stand that is greater than a footprint of the cap of the container.

7. The combination dispenser and container of claim 6, wherein said means for attaching said dispenser to said second part of said cap includes a peripheral lip extending from the top wall and side wall of said housing, wherein said peripheral lip and said top wall define a recess in which said second part of said cap is securely received.

8. The combination dispenser and container of claim 6, wherein said means for attaching said dispenser to said second part of said cap includes a peripheral lip extending from said second part of said cap and defining a recess in said second part of said cap in which said top wall and upper end of said side wall of said housing are securely received.

9. The combination dispenser and container of claim 6, wherein said means for attaching said dispenser to said second part of said cap includes an integral connection between said second part of said cap and said top wall and side wall of said housing.

10. A dental floss dispenser and toothpaste container device for holding and dispensing dental floss and toothpaste comprising:

a stand-up toothpaste container including an elongated flexible tube having a sealed tail at an upper end and a head at a lower end including a nozzle through which toothpaste may be dispensed;

a two-part flip-open cap coacting with the head for selectively opening and closing said nozzle, said cap including a first part removably attachable to said head and a second part, said first part having a spout aligned with said nozzle on said head of said container to direct the flow of toothpaste from said nozzle through said spout and said first part of said cap, said second part being hingedly attached to said first part to facilitate movement of said second part between open and closed positions, said second part including closure means for engaging said spout in said closed position thereby preventing toothpaste from flowing from said spout, a dental floss dispenser having a housing including top, bottom, and side walls defining a chamber for storing dental floss, and an opening in the housing for dispensing floss, said opening being in said top wall;

means for severing said dental floss; and means for removably attaching said dental floss dispenser to said second part of said cap, whereby said container, cap, and said dispenser are adapted to stand in an upright position on said dispenser when said second part is in said closed position, said second part of said cap including an opening coacting with the opening in said housing to dispense said dental floss, whereby said second part of said cap must be in the open position to dispense the dental floss.

11. A dental floss dispenser and toothpaste container device for holding and dispensing dental floss and toothpaste comprising:

a stand-up toothpaste container including an elongated flexible tube having a sealed tail at an upper end and a head at a lower end including a nozzle through which toothpaste may be dispensed;

a two-part flip-open cap coacting with the head for selectively opening and closing said nozzle, said cap including a first part removably attachable to said head and a second part, said first part having a spout aligned with said nozzle on said head of said container to direct the flow of toothpaste from said nozzle through said first part of said cap, said second part being hingedly attached to said first part to facilitate movement of said second part between open and closed positions, said second part including means for engaging said spout in said closed position preventing toothpaste from flowing from said spout, a dental floss dispenser having a housing including top, bottom, and side walls defining a chamber for storing dental floss, said dental floss dispenser being attached to said second part of said cap, and said top wall of said dispenser and said second part of said cap including corresponding openings which coact to dispense said dental floss only when the second part of said cap is in the open position; and means for severing said dental floss, whereby said container, cap, and said dispenser are adapted to stand in an upright position on said dispenser when said second part is in said closed position.

12. The combination of a dental floss dispenser and a stand-up toothpaste container, said stand-up toothpaste container comprising:

flexible tube means for storing toothpaste and having a nozzle means at one end for selectively discharging toothpaste when pressure is applied to said tube means, and cap means coacting with the nozzle means for selectively opening and closing said nozzle means, said dental floss dispenser comprising:
    a housing means for storing dental floss, said housing means including a top wall, a bottom wall and side wall means, and means for dispensing and severing said floss from said housing,
    said means for dispensing and severing said floss including an opening in said housing means that is accessible for dispensing floss only when the cap means is positioned for opening said nozzle means, and means attaching said dental floss dispenser to said cap means, whereby said combination dispenser and container are adapted to stand in an upright position on the bottom wall of said dispenser.

\* \* \* \* \*

UNITED STATES PATENT AND TRADEMARK OFFICE
CERTIFICATE OF CORRECTION

PATENT NO.   : 5,979,706
DATED        : November 9, 1999
INVENTOR(S)  : Stephen M. Grussmark It is certified that error appears in the above-indentified patent and that said Letters Patent is hereby corrected as shown below:

Col. 7, line 62, change "CELp" to --cap--.

Signed and Sealed this

Twenty-third Day of May, 2000

Attest:

Q. TODD DICKINSON

*Attesting Officer*          *Director of Patents and Trademarks*